United States Patent [19]
Bourne

[11] Patent Number: 5,268,303
[45] Date of Patent: Dec. 7, 1993

[54] SAMPLE CONCENTRATOR/SOLVENT EXCHANGE SYSTEM

[75] Inventor: Sidney Bourne, Lexington, Mass.

[73] Assignee: Bio-Rad Laboratories, Inc., Hercules, Calif.

[21] Appl. No.: 43,315

[22] Filed: Apr. 6, 1993

Related U.S. Application Data

[62] Division of Ser. No. 776,926, Oct. 15, 1991, Pat. No. 5,238,653.

[51] Int. Cl.$^5$ .............................................. G01N 30/02
[52] U.S. Cl. .................................... 436/161; 210/656; 422/70; 422/101
[58] Field of Search ................... 422/70, 101; 436/161, 436/178; 210/656

[56] References Cited

U.S. PATENT DOCUMENTS

| | | | |
|---|---|---|---|
| 4,165,360 | 8/1979 | Casper et al. | 422/202 |
| 4,281,246 | 7/1981 | White et al. | 250/282 |
| 4,552,723 | 11/1985 | Adams et al. | 422/66 |
| 4,567,020 | 1/1986 | Lognet et al. | 422/101 |
| 4,662,914 | 5/1987 | Hansen et al. | 55/386 |
| 4,695,555 | 9/1987 | O'Keeffe | 436/150 |
| 4,699,768 | 10/1987 | Weiss | 422/70 |
| 4,740,298 | 4/1988 | Andresen et al. | 210/198 |
| 4,801,430 | 1/1989 | Albert et al. | 422/101 |
| 4,824,792 | 4/1989 | Thorpe et al. | 422/70 |

OTHER PUBLICATIONS

Christensen et al., *Anal. Chem.* (1981) 53:171-174.
Christensen et al., *Chromatographic Reviews,* Elsevier Science Pubs. B.V., Smsterdam, The Nethrlands (Date Unkn) pp. 61-70.
Fujimoto et al., *Chromatographia* (1987) 23:512-516.
Hellgeth et al,, J. Chrom. Sci. (1986) 24:519-528.
Griffiths et al., "Solvent Elimination Techniques for HPLC/FT-IR," (Date Unknown) pp. 105-138.
Bio-Rad Sales Brochure, "HRLC TM: The New Generation in HPLC," 1986.

*Primary Examiner*—James C. Housel
*Assistant Examiner*—Lien Tran
*Attorney, Agent, or Firm*—Townsend and Townsend Khourie and Crew

[57] ABSTRACT

A liquid concentrator method provides for a guide rod (1) around which solution flows, in a chamber (2). A heat source (3) surrounds the guide rod. The solution is preferably mixed with; an exchange solvent, the exchange solvent having a higher boiling point than the solution solvents. As the mixture flows down the guide rod, the original solvents are preferably evaporated, concentrating the materials of interest, and leaving the effluent relatively more concentrated in the exchange solvent.

6 Claims, 2 Drawing Sheets

SAMPLE CONCENTRATOR/SOLVENT EXCHANGE SYSTEM

This is a division of application Ser. No. 07/776,926, filed Oct. 15, 1991, now U.S. Pat. No. 5,238,653.

BACKGROUND OF THE INVENTION

The present invention relates to manipulation of materials dissolved in solvents. More specifically, in one embodiment, the invention provides an improved continuous flow interface for a liquid chromatograph.

Liquid chromatography systems and their use are well known to those of skill in the art. In a liquid chromatography system, a mixture of materials is separated for analysis. The mixture is dissolved in a suitable solvent and injected into the top of a column packed with a suitable adsorptive material. As the material flows through the column, the various materials are adsorbed to the packing at different rates such that the eluents emerging from the bottom of the column are spatially separated with the less highly adsorbed materials generally leaving first and the more highly adsorbed materials leaving later.

It is often desirable to remove the solvent from the separated components, since the solvent can interfere with post-separation work with the components. This work might involve chemical or instrumental analysis, or chemical reactions of the components. For example, it is often desirable to flow the effluent from the column into an IR spectrometer for analysis. One set of techniques has involved passing the effluent from the chromatograph through a flow cell and measuring the infrared transmission spectra of the separated components. One problem with this technique is that the solvent typically has an absorption spectrum that must somehow be subtracted out of the measured spectra. Depending upon the particular materials and solvent involved, this is sometimes difficult or impossible to fully resolve. An alternative process for obtaining spectra involves removing the solvent from the effluent and taking spectra of the residual sample materials.

A variety of techniques for elimination of part or all of the LC solvent in a LC effluent have been proposed, some of which are described in Griffiths et al., "Solvent Elimination Techniques for HPLC/FT-IR," incorporated by reference herein for all purposes. It is often desirable to provide material to such devices at relatively constant flow rates or solvent composition. This problem has been difficult to resolve. Another technique, which has been proposed for use as a concentrator in a liquid chromatography mass spectrometry interface, is described in White et al., U.S. Pat. No. 4,281,246. This technique provides for a system in which LC solvent flows down a heated wire. As the effluent flows down the wire, solvent is preferentially evaporated, resulting in an effluent which is more highly concentrated in the materials of interest.

While meeting with substantial success, certain problems remain with the system of White et al. for removing solvent from a LC effluent. For example, (1) band broadening: time resolution of the LC peaks is not maintained; (2) special broadening: material is spread into too large an area; (3) the effluent has insufficient concentration.

One source of these problems is the inability to achieve an uniform flow rate through interface. The difficulties in non-uniform flow stem, in part, from the nature of the wire guides used in the interfaces. First, these wire guides have problems with wetability, preventing the liquid from forming an even coat over the guide. Second, using the wire guide itself as a heat source causes it to become hotter than the surrounding liquid. When the liquid reaches its boiling point, it evaporates off the wire and leaves dry spots. Without liquid to cool the wire, the temperature of the dry spot increases further. When liquid hits one of these local dry spots it immediately sputters off, making it impossible to obtain a uniform liquid coat over the surface. The uniform flow problem is further exacerbated by the non-uniform multiple stages of the wire described in the prior art. These guide wires have stages with decreasing diameter and resistance. At the transition points between stages, the liquid tends to form beads. These difficulties with obtaining a uniform flow over the guide limit the minimum flow rate achievable, and consequently, decrease the concentration that the wire guide based interfaces can achieve.

Another problem with the prior art concentrator system of White et al. is the feedback control system. The response of the drop-size monitor is too slow to be effective when the solvent changes in composition, as commonly occurs during solvent programming in liquid chromatography.

From the above it is seen that an improved sample concentrator between a liquid chromatograph and a second system such as an IR analysis device is needed.

SUMMARY OF THE INVENTION

An improved liquid concentrator/solvent exchange system is provided by virtue of the present invention. As an example application, the invention provides for an effluent concentrator into which effluent from a liquid chromatograph flows. The effluent is concentrated in materials of interest, and the proportion of solvent is decreased in the concentrator. The effluent from the LC is preferably mixed with an exchange solvent, the exchange solvent being a different solvent from the solvent used in the liquid chromatograph and having a higher boiling point (lower vapor pressure) than the liquid chromatograph solvent.

The effluent flows down the heated guide rod, which is preferentially heated, by a coiled wire. The solvents are evaporated off the rod-by the heat generated by the coil, concentrating the materials of interest, and leaving the effluent substantially more concentrated in the exchange solvent. Next the effluent is drawn off the rod through a tube, and may then be analyzed in, for example, an infrared analyzer.

Accordingly, in the preferred embodiment, the invention provides an interface for removal of a solvent from effluent. The system includes a body defining a chamber; a guide rod extending from a first end of the chamber to a second end of the chamber; a heat source for heating a region surrounding the guide rod thereof; and a chromatographic input for flowing chromatographic effluent and an exchange solvent down an exterior wall of the guide rod.

In another embodiment, the interface replaces the rod and heating coil with a wire extending from a first end of said chamber to a second end of said chamber and a means for supplying a potential difference across said wire for heating of at least a portion thereof.

A further understanding of the nature and advantages of the inventions herein may be realized by reference to the remaining portions of the specification and the attached drawings.

DESCRIPTION OF THE PREFERRED EMBODIMENTS

Figure 1:
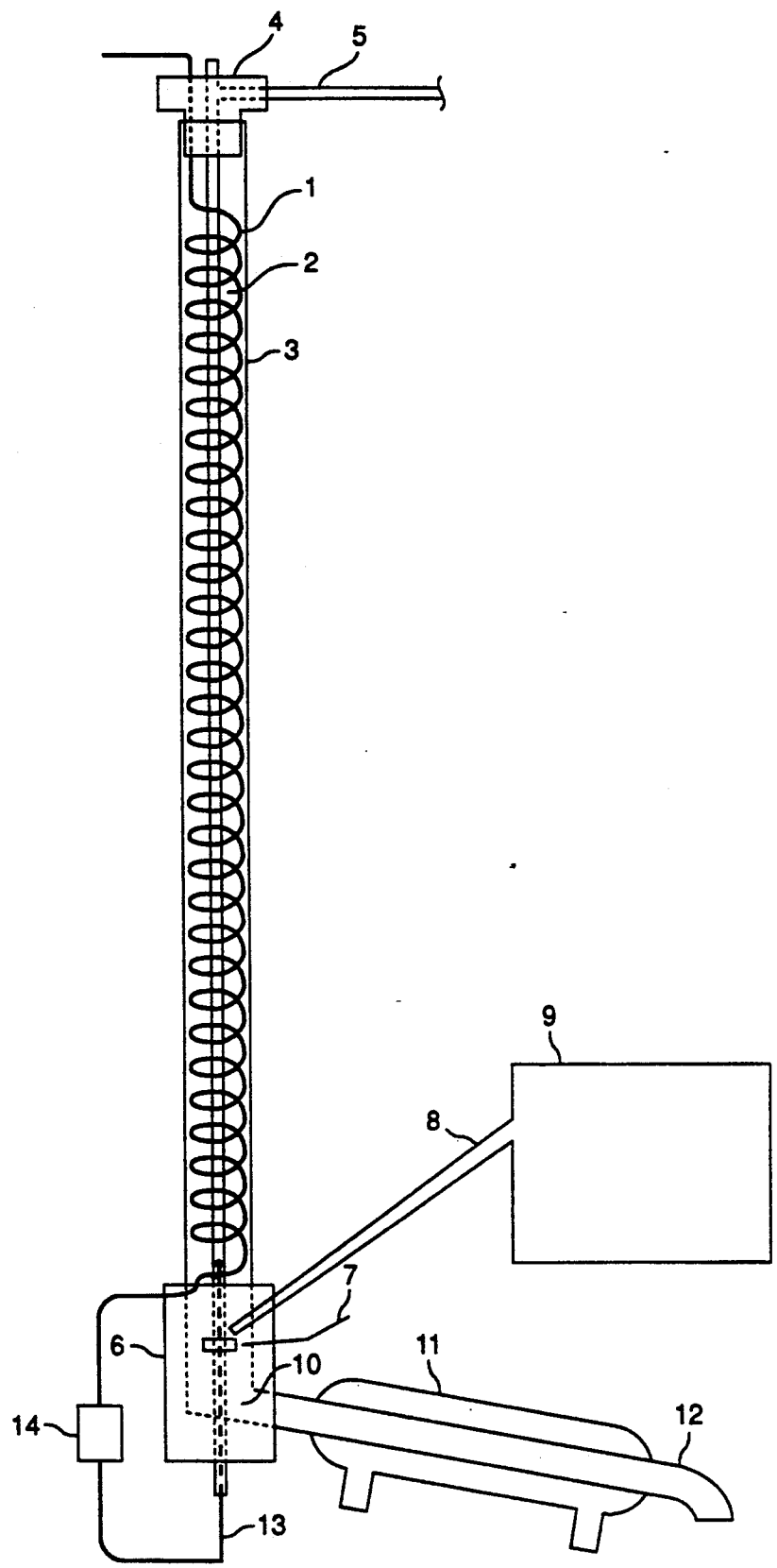
FIG. 1 is a cross-sectional view of the liquid concentrator disclosed as a first, preferred, embodiment herein.

FIG. 1 illustrates a preferred concentrator system for processing effluent from a liquid chromatograph. The interface includes a glass guide tube 1, about 100-cm long and 1-mm OD in a preferred embodiment, held in a vertical position. The surface of the glass guide has preferably been etched by treating it with a hot solution of KOH. This treatment increases the wetability of the guide.

The entire length of the guide is surrounded by a coaxial heating coil or wire 2, with a coil ID of 6 to 8-mm in a preferred embodiment. The coils may be evenly spaced, or optionally, may be closer together at the top than at the bottom, in order to give more heating power towards the top of the guide than towards the bottom.

A heater support 3 houses the guide and the coil. The heater support is glass tube of about 8-mm ID in a preferred embodiment. Outside the heater support may optionally be additional thermal insulation.

A fitting, including a concentrator cap 4 with a liquid stream inlet tube 5, mounts on top of the heater support tube. In the preferred embodiment, the fitting has a center vertical aperture through which the guide passes, and a hole for the sample solution. The fitting functions to direct the sample flow down around the outside of the guide as it flows into the device by way of the inlet tube.

The exchange solvent is preferably mixed with the solvent in a tee upstream of the concentrator. optionally, there are two inlets to the concentrator and top fitting, one for the exchange solvent, with the mixing being done in the top fitting.

The concentrator cap is preferably made from a material that provides a clean, inactive surface for the sample solution to contact, such as Teflon. The outlet of the concentrator cap is designed to fit within a few tenths of a mm around the guide rod. The outlet port is preferably pointed-so that it empties into the chamber, minimizing surface area for the solvent to cling to. This design allows the solvent to flow smoothly onto the guide.

The heater support housing 3 mounts into a bottom fitting 6. The bottom fitting houses the sample collection point, which is where the concentrated sample is drawn off the guide rod. The guide rod passes through the bottom fitting, being held in place and sealed by a compression fitting. A collection ring 7 fits snugly around the guide rod at a collection point in the base. It causes the concentrated sample solution to bead up off of the surface of the guide.

A draw-off tube 8 passes through a hole in the side of the bottom fitting, and intersects the guide at the sample collection point at about a 45-degree angle from above. The draw-off tube is made of such material as fused silica or Teflon in a preferred embodiment. It is typically of narrow ID, about 0.15-mm, and may serve, for example, as a flow restrictor to control the flow from the collection point to the exit of the concentrator, or to an IR spectrometer 9.

Other means of controlling the flow from the draw-off tube may be used. The draw-off tube may be attached to a restrictor, which empties into a vacuum chamber. Another possible approach would be to have the entire system sealed, including the waste reservoir. Flow would then be controlled by maintaining the collection point slightly above atmospheric pressure. A constant flow pump in the outlet stream in place of the restrictor would be another way to control the flow.

Below the sample collection point, a drain port 10 allows both liquid and vapor solvent to pass into the top of a condenser 11. The condenser is preferably a standard water-cooled jacketed solvent condenser. It serves to condense and collect the solvent coming from the concentrator, and deliver the residue to a collection flask via an outlet 12. The bottom fitting preferably has viewing windows in line with the sample collection point.

A thermocouple 13 is optionally inserted up the center of the guide to a point near the bottom of the heater. The thermocouple is used to monitor the surface temperature of the guide, supplying a feedback signal which is used to control the heater current. Both the heating coil and thermocouple are connected to a temperature controller 14, which supplies the current to the heating coil.

Use of an extraction/exchange solvent provides an output solution of uniform flow rate and composition. A uniform outlet solvent may be critical to the performance of the detector, which accepts the flow from the concentrator.

The exchange solvent should have a higher boiling point than any of the solvents used during the separation. Preferably, it should be moderately polar, so that it dissolves any substrates of interest at a concentration of about 0.1% or lower. Optimally, the solvent will be of low toxicity and easy to dispose. An example of such a solvent is 2-methoxyethanol.

In operation, the user first begins the flow of cooling water through the condenser. LC effluent is mixed with the exchange solvent in a mixing tee or chamber, and then flows into the concentrator cap. The incoming mixture then evenly wets the guide rod, flowing downwards thereon. As the mixture flows down the rod, it is heated by the surrounding coil. The LC solvent is preferentially evaporated from the mixture, leaving the mixture more concentrated in the exchange solvent. The concentrated mixture is then drawn off the rod via the draw-off tube, preferably at a constant rate. Any excess liquid flows over the collection ring and is collected along with condensed LC solvent, in the condenser.

Another option is to have multiple stage concentrators. For example, in a two stage concentrator, the top stage would concentrate the original LC effluent down to about 0.1to 0.2-mL/min, with or without exchange solvent. The discharge of the top stage would preferably feed the top of the next stage. Optionally, exchange solvent would be added at about 1-mL/min at the transition point, and the total flow would be concentrated by the next stage. This multiple stage system permits a coarse control for the first stage, which can accommodate a wide range of solvent compositions and flow rates. The input to the subsequent stages, being mainly exchange solvent would be more uniform. The more uniform composition of the input permits a finer control and more concentration in the subsequent stages.

The preferred embodiment has several advantages over the prior art. It removes a number of sources of irregular liquid flow that limit the flow rate and concentration capability of the concentrator. For example, metal wire typically has poor wetting characteristics. In the preferred embodiment, the guide rod is made of glass which has a high surface tension. In preferred embodiments, the glass is, e.g., soda-lime glass, fused silica, quartz, borosilicate glass, or the like. Roughening or etching a glass guide rod, for example, by treating it with KOH further enhances its wetability. Consequently, the liquid spreads out and evenly coats the guide rod, rather than beading up on the surface. The wettability of the guide is of particular importance when water is the major component of the solvent. Water is the most commonly used LC solvent, and is also the most difficult to get to wet a guide rod.

The use of a single stage guide, rather than a set of different stages of decreasing diameter, avoids the problem of the liquid beading up at transition points. Using a heat source other than resistance across the guide itself avoids the problems associated with overheating and dry spots. In the preferred embodiment, the guide rod serves only as a guide; the coaxial heating coil heats the gas around the guide to promote evaporation. Consequently, the guide rod is often cooler than the liquid flowing down it, substantially reducing the formation of dry spots.

The thermocouple permits fine and rapid temperature control of the guide rod. Temperature control is further facilitated by placing the thermocouple in the guide near the bottom of the heating coil, where the temperature should be just below the boiling point of the exchange solvent, and where flow should be at its lowest. When the thermocouple is used, a hollow glass tube is used as a guide instead of a glass rod. The thermocouple is inserted into the tube, while the solvent runs down the outside surface. This system maintains the correct temperature and avoids overheating the guide and causing dry spots.

Another advantage of the invention is that it permits a relatively simple method to measure flow rate: by measuring temperature. Using this exchange solvent system, one may use the temperature of the guide surface as an indicator of the flow rate past that point. Preferably, the temperature of the solvent is measured at a point near the base of the concentrator, and it should be near the solvent's boiling point. Because the solvent at the base of the concentrator is mainly residual exchange solvent, it is relatively uniform in composition over the chromatographic run, the boiling point is stable, and the temperature of the guide rod surface at the base correlates to the residual flow rate.

Figure 2:
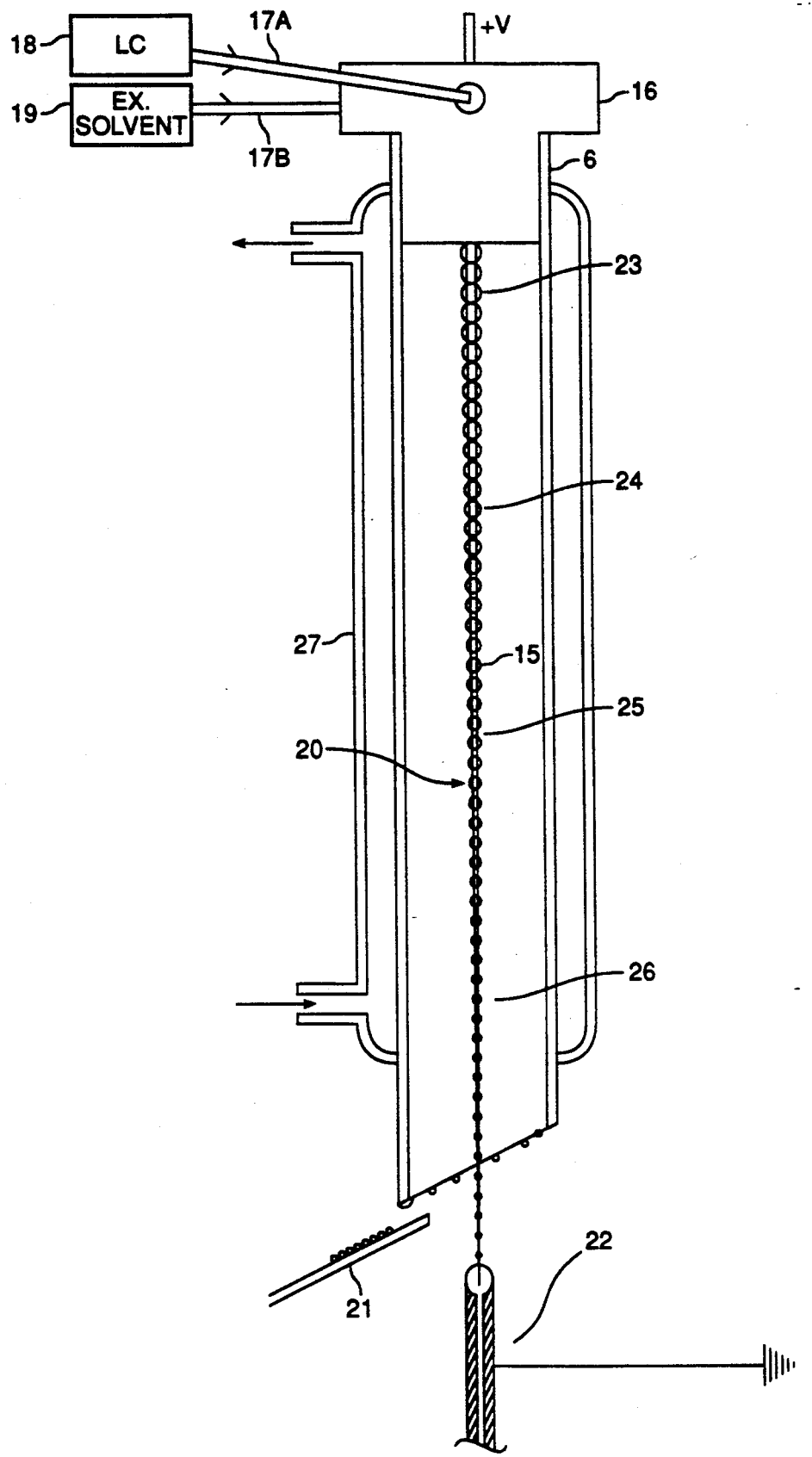
FIG. 2 is a cross-sectional view of another concentrator system.

In a second embodiment, illustrated in FIG. 2, effluent from the LC and the exchange solvent flows down a wire which is heated by application of a potential difference there across. The wire passes through a cooling chamber, which is preferably a jacketed, water cooled condenser 27.

The top portion of the main body is enclosed by a mixing cap 16. The mixing cap contains inlets 17a and 17b for inputting effluent from the LC 18 and a source of exchange solvent 19, respectively. The mixing cap is made of, for example, Teflon. The outlet of the mixing cap is directed downward into the main chamber 15, and is affixed in a relatively close relationship with wire 20 such that exiting fluid from the mixing cap flows down the wire.

The bottom portion of the main body is open, and preferably cut at a skewed angle such as about 10°–45° for easier collection of solvent condensed within the chamber 15. A solvent collector 21 is provided below the lowest point on the main body for collection of condensed solvent.

A heating wire 20 extends through the mixing cap, along the length of the chamber 15, generally through the center thereof, and out the bottom of the main chamber where it is connected to the inside of an effluent receiving tube 22. The upper end of the wire is directly or indirectly coupled to the output of the mixing cap such that liquid which is exiting the mixing cap flows down the wire. The effluent receiving tube is connected to, for example, a vacuum chamber for infrared analysis equipment, or the like.

The upper end of the heating wire 20 is connected to a first electrical potential, while the lower end of the heating wire, via the tube 22, is connected to a second potential such as ground. The potential difference may be generated by, for example, a voltage source such as a battery or transformer, a current source, or the like. Accordingly, current is forced to flow through the heating wire, and the resistance therein creates heat along the length of the wire so as to cause evaporation of the solvent therefrom. An upper portion of the heating wire 23 is of a relatively large diameter, low resistance metal such as copper which extends through the mixing cap and a short distance into the main chamber. According to one embodiment the upper section of the wire is 0.032-inch diameter copper wire. This section of wire is of relatively low resistance, and will generate relatively little heat so as to prevent boiling and associated splattering from occurring within and near the mixing cap (along with the attendant errors generated in the analysis of such backmixed fluids), and also allowing smoother flow and less band broadening. A second section of wire 24 is of relatively higher resistance, allowing greater heating along its length and is formed of, for example, 0.032-inch nichrome. A third portion of the wire 25 is of smaller diameter and lower resistance such as 0.020-inch alumel, while a fourth portion of the heating wire 26 is of still smaller diameter and resistance such as 0.012-inch copper. The smaller diameter wires near the bottom of the main chamber provide for improved flow characteristics down the length of the wire.

The entire length of the wire is appropriately treated to improve its wetting capabilities vis-a-vis the effluent/solvent mixture, such as by etching with KOH solution, or by treating with polyethylene glycol followed by heating and washing.

A single stage interface is shown in FIGS. 1 and 2, but in some embodiments, additional stages are provided for improved performance. In such multi-stage systems, the first stage will reduce the effluent volume to, for example, 0.1 mi/min and this is passed to the top of a second stage where an additional 1.0 mL/min of exchange solvent would be added. The second stage would then again reduce the flow to about 0.05 to 0.1 mL/min and will produce an output which is relatively much more rich in exchange solvent.

In operation, the user starts cooling flow through the cooling water jacket, in some embodiments using conventional tap water and in other embodiments using a chilled water supply. The flow of extraction solvent is then started, followed by the flow of LC effluent. In general, the flow rate of LC solvent is about 0.5 to 3 ml/min and, in such embodiments, the flow of extraction solvent is generally selected to be about 0.5 to 1 ml/min, although a wide range of flow rates will be used according to some embodiments of the invention. The extraction solvent and LC effluent are mixed in the mixing cap and flow down the wire 20. On the first section of wire 23 very little or no heating occurs, and in any event insufficient heating occurs to create boiling of the liquid thereon. In the second section of wire 24, greater heating occurs, causing evaporation of the solvent used in the liquid chromatograph as well as a lesser relative amount of the exchange solvent.

Very little evaporation of the materials of interest in the LC effluent will take place. Since the exchange solvent has a higher boiling point (lower vapor pressure) than the liquid chromatograph solvent, relatively greater amounts of liquid chromatograph solvent will evaporate from the effluent.

As the fluid flows down the wire to the third section 25, it encounters a smaller diameter section, which will be appropriate for flow of the now smaller volume of liquid flowing thereon.

The fluid then encounters the fourth section of wire 26, which has lower resistance, and reduces evaporation before exiting the system. The fluid then enters the tube 22, where it flows to the next analysis device such as an IR analysis device.

As solvent evaporates from the wire, it will enter the vapor space in the chamber 15. The vapors will be cooled by the walls of the main chamber, collected thereon in droplets, and will flow to the bottom of the tube where the droplets will be collected by solvent recovery drain 21 for reuse or disposal.

The above description is illustrative and not restrictive. Many variations of the invention will become apparent to those of skill in the art upon review of this disclosure. Merely by way of example while the invention is illustrated primarily as an interface to an infrared analysis device, the interface could be used as a concentrator for other devices. The scope of the invention should, therefore, be determined not with reference to the above description, but instead should be determined with reference to the appended claims along with their full scope of equivalents.

What is claimed is:

1. A method of concentrating LC effluent with an exchange solvent wherein said LC effluent contains an original solvent, said method comprising the steps of:
   a) adding to said LC effluent a exchange solvent;
   b) directing said LC effluent together with said exchange solvent down an exterior of a guide rod;
   c) heating said guide rod with a heat source around said guide rod to thereby evaporate said original solvent; and
   d) collecting an exchange solvent concentrated effluent from a bottom region of said guide rod.

2. The method as recited in claim 1 wherein said step of heating is a step of supplying current to a heating coil surrounding said guide rod.

3. The method as recited in claim 1 wherein the step of collecting is a step of directing said exchange solvent concentrated effluent over a ring around said guide rod and drawing said exchange solvent concentrated effluent off of said ring with a draw-off tube.

4. The method as recited in claim 3 wherein said step of drawing off is a step of drawing off at a substantially constant rate, excess exchange solvent concentrated effluent flowing over said ring.

5. The method as recited in claim 1 further comprising the step of condensing said evaporated solvent in a condenser.

6. The method as recited in claim 1 further comprising measuring a flow rate of said concentrated effluent by measuring the temperature of said guide rod.

* * * * *